United States Patent [19]
Ranoux

[11] Patent Number: 4,902,286
[45] Date of Patent: Feb. 20, 1990

[54] CONTAINER FOR FERTILIZATION OF HUMAN OVOCYTES IN THE ABSENCE OF $CO_2$-ENRICHED AIR

[76] Inventor: Claude Ranoux, 7 Rue des Grands Champs, 77330 Lesigny, France

[21] Appl. No.: 80,537
[22] PCT Filed: Nov. 7, 1986
[86] PCT No.: PCT/FR86/00378
§ 371 Date: Jul. 6, 1987
§ 102(e) Date: Jul. 6, 1987
[87] PCT Pub. No.: WO87/02879
PCT Pub. Date: May 21, 1987

[30] Foreign Application Priority Data
Nov. 8, 1985 [FR] France .................. 85 16558

[51] Int. Cl.⁴ .............................. A61B 19/00
[52] U.S. Cl. .................. 604/403; 600/33; 600/34; 435/296
[58] Field of Search .......... 600/33, 34; 604/328, 604/330, 403; 128/341, 343, 769, 778; 435/1, 296, 299; 220/258

[56] References Cited

U.S. PATENT DOCUMENTS

| | | | |
|---|---|---|---|
| 1,877,766 | 9/1932 | Kennedy | 128/341 |
| 2,456,607 | 12/1948 | Shaffer . | |
| 2,707,471 | 5/1955 | Koff | 128/341 |
| 2,818,064 | 12/1957 | Leff | 128/834 |
| 3,239,429 | 3/1966 | Menolasino et al. | 435/296 |
| 3,805,784 | 4/1974 | Alter . | |
| 3,875,012 | 4/1975 | Dorn et al. | 435/296 |
| 4,300,544 | 11/1981 | Rudel | 128/832 |
| 4,380,997 | 4/1983 | Leibo . | |
| 4,427,477 | 1/1984 | Milgrom | 128/837 |
| 4,533,345 | 8/1985 | Louw . | |
| 4,555,037 | 11/1985 | Rhees | 220/258 |
| 4,579,823 | 4/1986 | Ryder | 435/296 |
| 4,598,045 | 7/1986 | Masover et al. | 435/296 |
| 4,747,500 | 5/1988 | Gach et al. | 220/258 |
| 4,761,379 | 8/1988 | Williams et al. | 435/296 |

FOREIGN PATENT DOCUMENTS

| | | | |
|---|---|---|---|
| 43002 | 2/1930 | United Kingdom | 604/403 |
| 558998 | 1/1944 | United Kingdom | 604/403 |
| 2158093 | 11/1985 | United Kingdom | 435/296 |

Primary Examiner—C. Fred Rosenbaum
Assistant Examiner—Mark O. Polutta
Attorney, Agent, or Firm—Young & Thompson

[57] ABSTRACT

The invention relates to a container for fertilization of human ovocytes in the absence of $CO_2$ which may be done in an incubuator at 37° C. or in the vaginal cavity. The container of cylindrical shape has smooth and rounded walls 1 whose thickness is 2 mm in the body 2 of the cylinder but only 1 mm at the neck 3. On the outer wall of the neck is seen a screwthread 4 permitting external screwing on of the plug 12 whose sides are smooth and rounded. The blind end 5 of the container is rounded, the other 6 is flat and has a round orifice 7, which orifice is closed by a fine membrane 9 permitting hermeticity of the tube in order to avoid disorders of the culture medium 8 present in the container as of manufacture. Above the liquid remains about 200 $\mu$l of gas 10. The inner walls 11 are smooth and rounded. After depositing the ovocytes and spermatozoa necessary for fertilization, and therefore after rupture of the membrane, hermeticity will be effected by two seals, after screwing on the plug, a circular one 13 at the neck of the tube, the other 14 on the endwall of the plug which will be flattened against the orifice of the tube 7 by a relief portion, located on the endwall of the plug 15, whose diameter is substantially that of the orifice. The container will be held in the posterior fornix of the vaginal cavity by a flexible ring comprised of a metal strip 17 sheathed in rubber 18 to which is fixed a rubber pouch 19 in which the container is placed.

This device thus permits inter-vaginal, fertilization of human ovocytes in the absence of $CO_2$-enriched air, the vaginal cavity replacing the incubator conventionally used.

30 Claims, 2 Drawing Sheets

CONTAINER FOR FERTILIZATION OF HUMAN OVOCYTES IN THE ABSENCE OF $CO_2$-ENRICHED AIR

This invention concerns a totally new procedure for fertilizing human ovocytes, making use of a device that we will describe.

In vitro fertilization of human ova is a very complex technique which permits a solution for cases of infertility of couples which up to then were irreversible. Since the first birth, of Louise Brown, in 1978, achieved by the Edwards team in England, thousands of children have been born worldwide through this technique.

The major concern of all teams working in vitro fertilization has always been to obtain a simplification of the technique while maintaining or improving the results. Thus from the clinical standpoint there has appeared:

stimulation to obtain a plurality of ovocytes thereby increasing the chances of success, methods of ovarian puncture other than under coelioscopic control, namely under transvesical, then transvaginal and finally transurethral ultrasonic control which enabled general anesthesia to be eliminated and possible $CO_2$ toxicity to be avoided. From the biological standpoint the freezing of supernumerary embryos has permitted an improvement of results. Only the biological stage of fertilization per se has undergone but minimal changes.

It has remained very complex to date. Conventionally it involved aerobic or sterile culturing of embryos in a box or tube at 37° C. and under a 5% $CO_2$ atmosphere. This requires non-hermetically sealed boxes or tubes with a risk of contamination by the surroundings. Hence the need for a $CO_2$ incubator (developed by "Testart") perfectly controlled at 37° C. and in $CO_2$. This equipment is cumbersome and expensive.

Similarly, initially, after puncture, one proceeded to a 1-to-4 hour maturation phase of the ovocytes in a culture medium usually enriched with human serum and, after this period, the fertilization of the ovocytes, changing the medium 18 to 24 hours after the stripping of the ova was effected. (This stripping involves the mechanical removal of the cumulus surrounding the ovum to observe the stage of development.) The ovum was then transferred to a new medium which after 20 to 24 hours was again changed before transfer into the uterine cavity, which involved the use of more than 3 ml of culture medium per ovum and numerous manipulations spread over 48 hours, which could be toxic to the ova.

The procedure that we have developed and whose scientific steps we will summarize is characterized by its simplicity and savings in time and money.

This procedure comprises fertilization of human ovocytes in the absence of $CO_2$-enriched air with the help of a fluidtight tube completely filled with culture medium that is placed in the vagina cavity which then serves as an incubator. Upon puncture of the ovocytes which was delayed (so as to avoid the ovocyte maturation phase), they are placed in the container along with the spermatozoa necessary for fertilization which were previously prepared. Then the device with its holding means is placed in the vaginal cavity from where it will be removed 44 to 48 hours later in order to reintroduce the ova in the uterine cavity by means of a "Frydman" catheter.

The invention will be better understood by consideration of the following description, taken in connection with the accompanying drawings, in which.

Figure 1:
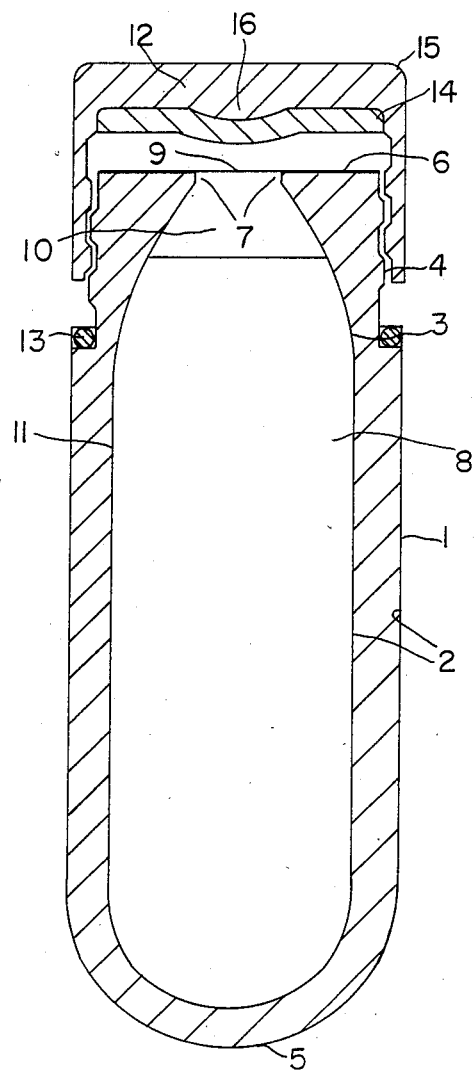
FIG. 1 is a cross sectional view of a container according to the present invention.

We are going to describe an embodiment of the container which constitutes the device (FIG. 1).

It is cylindrical tube of small dimensions, with smooth and rounded outer walls (1) in order to avoid any trauma to the vaginal mucosa. Its approximate dimensions are 4 cm long and 1.5 cm outer diameter; the thickness of the walls is 2 mm for the body (2) of the cylinder except in the region of the neck (3) where it is not more than only 1 mm, which gives an inner cavity of 1.1 cm in diameter and 3.8 cm long with an effective volume of about 3.2 $cm^3$. This volume is suitable for the culture of 4 to 5 embryos. For a number of embryos greater than five, the volume of medium used may be increased to 5 $cm^3$, the outer dimensions will then be 4.5 cm long and 1.7 cm outer diameter, the thickness of the wall remaining the same. Likewise shapes other than the cylindrical shape can be envisaged: round, archlike or pear-shaped depending on the configuration of the vagina.

On the outer wall of the body of the tube a marking surface must be provided for the patient's name. On the outer wall of the plug a screw limits aseptic defects.

Due to the decrease in the thickness of the wall of the neck, the outer edge of the plug, once it is screwed on, does not protrude beyond the wall of the tube.

The blind end (5) of the tube is rounded.

The upper end (6) of the tube adjacent the neck is flat and has at its center a round orifice (7) of about 4 mm in diameter. The ovocytes and the spermatozoa necessary for fertilization will be deposited through this orifice. The dimensions of the orifice has been purposely reduced in relation to the diameter of the tube in order to limit the communication between the culture medium and the surrounding atmosphere and therefore to minimize disorders caused thereby.

To reduce further septic risks, the medium disorders and the length of handling time, it seemed advisable to us to devise containers in which the culture (8) medium is placed in the tube at the time of its manufacture.

To avoid biochemical disorders to the medium between the time of manufacture and use, a hermetic closure of the tube will be effected by a thin membrane (9) covering the orifice. This membrane will be made so as to rupture easily when the ovocytes (22) and spermatozoa (24) are deposited in the tube by means of a glass "Pasteur pipette" (21, 23) or a throwaway plastic pipette end piece. Other types of sealed closure may be used such as a device with a valve.

The culture medium may be one of those conventionally used and marketed. The one that we use is the "I.N.R.A. de Menezo" medium marketed under the name "B2" by "A.P.I. Systeme". There will remain only a small volume (10) of gas of about 200 $\mu$l between the surface of the medium and the membrane, corresponding to the volume of the ovocytes and spermatozoa transferred.

The inner walls (11) of the tubes must be perfectly smooth and rounded to avoid one of the ova remaining attached when they are removed and transferred to the uterine cavity.

The plug (12) of about 1 cm in height by 1.5 cm in diameter will be screwed onto the neck of the tube to close off the orifice. After rupturing the membrane, perfect fluidtightness is, however, necessary to avoid medium disorders and possible contamination resulting from it being placed in the vaginal cavity. This fluidtightness will be ensured by two seals, one (13) annular, gripping the neck of the tube, about 1 mm thick, the other (14) flat and round overlying the end wall of the plug, of identical thickness. To perfect fluidtightness, the underside of the plug has a relief portion (16) whose diameter is substantially equal to that of the orifice and which enables, when the plug is screwed on, the seal to be applied against the mouth of the orifice of the tube.

The outer wall of the plug has rounded edges (15).

The manufacturing material used will be a rigid plastic having a high mechanical strength (in case of trauma), of the polypropylene type, and non-toxic to cell cultures.

Figure 2A:
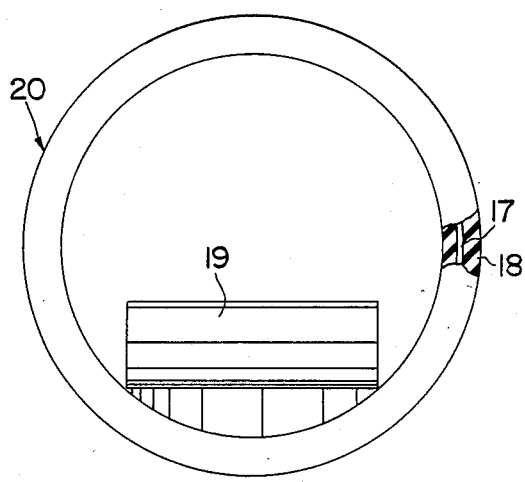
FIG. 2A is an elevational view of a pouch and ring for maintaining the container of FIG. 1 in place.
Figure 2B:
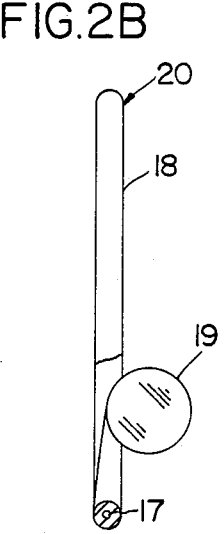
FIG. 2B is an edgewise view, partly broken away, of the structure showing in FIG. 2A.

The tube and the sterile medium will be individually packed in a sterile package of the cellophane paper type; at the time of packing the plug will not be completely tightened in order to avoid rupturing the membrane. A holding device (20) for maintaining the tube in the vaginal cavity is illustrated in FIGS. 2A and 2B. This device (20) comprises a flexible ring made of a metal strip (17) sheathed in rubber (18) to which is attached a small rubber pouch (19) the size of the tube and permits the tube to be slid therein. The diameter of the ring will be determined, like a diaphragm, for each patient individually as a function of the size of the uterine cavity and cervix at a consultation prior to in vitro fertilization. This device enables the holding of the tube in the posterior fornix of the vagina without risk of loss, or cooling of the culture medium due to a position too close to the vaginal introitus.

Figure 1A:
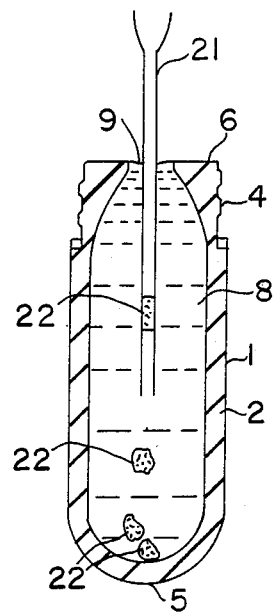
FIGS. 1A and 1B are schematic views showing the methods of using the container of FIG. 1.
Figure 1B:
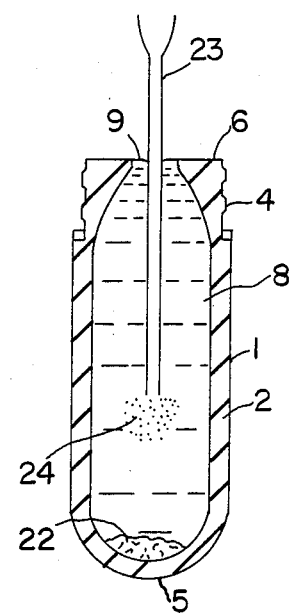

FIGS. 1A and 1B illustrate the insertion of pipettes (21, 23) through the membrane (9) to introduce ovocytes (22) and spermatozoa (24) respectively.

The approach which enabled us to develop this technical procedure and the device is based on findings and work research. The first such finding observed over six months was that a fraction of culture medium kept in a sterile, hermetically sealed (air-free to the extent possible) enabled it to be preserved for more than 10 days without disorders, and without its use changing the results conventionally obtained. The second finding is based on fertilization studies of three ovocytes placed in the same box well, that is, with 1 $\mu$l of medium; it demonstrates a cleavage rate identical to that obtained conventionally when a single ovocyte is cultivated per well. Also, the fact that if an ovum is left 48 hours in the same medium necessary for fertilization, this does not interfere with its stage of development.

Finally, a multiplicity of studies including those carried out with "Menezo" showed very minor changes in the culture medium before and after fertilization.

The sum of these findings prompted us to do preliminary studies which, despite the small number of patients, ovocytes and ova involved, induced us to go foward, since the initial results were very encouraging.

A first study on eight patients who had more than four ovocytes per puncture was carried out. About half of the ova obtained were cultured conventionally, the other half were cultured in the hermetically sealed tube and incubated 48 hours. No difference in the cleavage rate was observed. Two patients became pregnant, which corresponds to the success rate conventionally obtained.

In a second group of eight patients also having more than four ovocytes per puncture, about half were conventionally cultured and the other half were placed inside the vagina in a tube containing ova. Here again, the cleavage percentage was substantially the same and even slightly better with the intra-vaginal technique. Five of these patients became pregnant.

Even though the groups are too small to perform statistical analysis and therefore it is too early to draw conclusions, these results are very encouraging and while continuing a comparative study of the conventional culture method with the intra-vaginal technique, we have started pure intra-vaginal cultures; with the first two attempts, one of them resulted in the start of a pregnancy.

The advantages are great and numerous: savings in time and manipulations thus reducing the septic risks and toxicity to ova. Substantial financial savings by reasons of a lesser quantity of medium and simple lab equipment. And most of all, by eliminting the necessity of an expensive $CO_2$ incubator. The operational simplicity enables a lab technicians to be quickly trained, and therefore widespread disemination of the technique. A fundamental psychological contribution is the patient feeling more directly involved in the fertilization of her ova. It is perhaps too soon to envisage, but the good early results obtained are possibly related to culturing being carried out at a temperature which varies in full periods of one day and one night which no incubator is able to reproduce at present. This thermal variation may, totally hypothetically, be playing an important role in the development of the ovum. This procedure also permits the transporation of the ovocytes and the embryons by the patient herself or in a receptacle specially designed for a stabilized temperature of 37° C.

I claim:

1. A container for in-vitro fertilization of ovocytes and intravaginal culture, said container being of a size and configuration suitable for accommodation in a human vagina, said container comprising a hollow body containing a culture medium suitable for use in fertilization and culture of human ovocytes and having an orifice, said hollow body having rounded inner walls that are smooth over their entire extent, rupturable sealing means closing said orifice and hermetically sealing off the interior of the hollow body containing culture medium, said rupturable sealing means when ruptured permitting the introduction of ovocytes and spermatozoa into the container body, and a closure means cooperable with the container body and adapted to overlie the orifice, and resealing means operatively disposed between the container body and the closure means for hermetically resealing the container after rupture of the rupturable sealing means and introduction of ovocytes and spermatozoa to permit in-vitro fertilization of the ovocytes and intravaginal culture, the container when hermetically resealed having rounded outer walls that are smooth over their entire extent.

2. A container according to claim 1, wherein said rupturable sealing means comprises a membrane covering said orifice.

3. A container according to claim 1, wherein internal threads are provided on the closure means and complementary external threads are provided on the container body.

4. A container according to claim 3, wherein said container body has a neck proximate an end of said container body adjacent said orifice, said external threads being defined on said neck.

5. A container according to claim 4, wherein said closure means comprises a plug having a depending side-wall, said internal threads being formed on said depending sidewall.

6. A container according to claim 5, said plug being of the same diameter as the body immediately beyond said neck.

7. A container according to claim 1, wherein a relief portion is formed on the underside of the closure means and has a diameter substantially equal to that of the orifice, said resealing means comprising a seal lining the underside of the closure means including said relief portion and being sealingly engageable with an endwall of the container body adjacent the orifice.

8. A container according to claim 5, wherein a relief portion is formed on the underside of the plug and has a diameter substantially equal to that of the orifice, and said resealing means comprises a seal lining the underside of the plug including said relief portion and is sealingly engageable with the endwall of the body adjacent the orifice.

9. A container according to claim 5, wherein said sidewall has a free edge, said container body having an annular shoulder beyond said external screwthreads relative to said orifice, said resealing means comprising an annular seal between said free edge and said annular shoulder.

10. A container according to claim 6, wherein said sidewall has a free edge, said container body having an annular shoulder beyond said external screwthreads relative to said orifice, said resealing means comprising an annular seal between said free edge and said annular shoulder.

11. A container according to claim 1, in combination with a holding device for maintaining the container in a posterior fornix.

12. A container according to claim 1, wherein the container has an effective volume of about 3.2 cm$^3$ to about 5 cm$^3$.

13. A container according to claim 1, wherein the container is approximately 4 to 4.5 cm long and approximately 1.5 to 1.7 cm in diameter.

14. A container according to claim 1, wherein the diameter of the orifice of the container is less than half that of the container at its end adjacent said orifice to minimize communication between the interior of the container and the surroundings when the ovocytes and spermatozoa are being introduced.

15. A container according to claim 1, wherein the internal cavity of the container is oval.

16. A container according to claim 1, wherein the end of the container remote from the orifice has a rounded surface.

17. A container according to claim 1, wherein the culture medium substantially entirely fills the internal cavity of the container.

18. A container according to claim 1, wherein the internal cavity has a volume of about 3.2 to 5 cm$^3$ and there is an empty space of about 200 µl.

19. Apparatus for in-vitro fertilization of ovocytes and intravaginal culture, comprising an intravaginal container of a size and configuration suitable for accommodation in a vagina, said container comprising a hollow body containing a culture medium suitable for use in fertilization and culture of ovocytes, said hollow body having rounded inner walls that are smooth over their entire extent, a closure means for hermetically sealing the container body, a wall portion of the container body being rupturable, the closure means being adapted to overlie the rupturable wall portion after rupture, and means for penetrating said rupturable wall portion to introduce ovocytes and spermatozoa into the container body containing the culture medium so as to permit in-vitro fertilization and intravaginal culture in the hermetically sealed container, the hermetically sealed container during said culture having rounded outer walls that are smooth over their entire extent.

20. Apparatus according to claim 19, wherein said rupturable wall portion is a membrane for initially closing off an orifice of the internal cavity of the container body containing the culture medium.

21. Apparatus according to claim 19, wherein internal threads are provided on the closure means and complementary external threads are provided on the container body.

22. Apparatus according to claim 21, wherein said container body has a neck proximate an end of said container body adjacent said rupturable wall portion, said external threads being defined on said neck.

23. Apparatus according to claim 22, wherein said closure means comprises a plug having a depending sidewall, said internal threads being formed on said depending sidewall.

24. Apparatus according to claim 23, said plug being substantially of the same diameter as the body beyond said neck.

25. Apparatus according to claim 23, wherein a relief portion is formed on the underside of the plug and has a diameter substantially equal to that of the orifice, and a seal that lines the underside of the plug including said relief portion and is sealingly engageable with the endwall of the body adjacent the rupturable wall portion.

26. Apparatus according to claim 23, wherein said sidewall has a free edge, said container body having an annular shoulder beyond said external screwthreads relative to said rupturable wall portion, an annular seal being disposed between said free edge and said annular shoulder.

27. Apparatus according to claim 19, wherein the rupturable wall portion is less than one-half the diameter of an endwall of the container body adjacent the rupturable wall portion.

28. Apparatus according to claim 19, further comprising a holding device for maintaining the container in the posterior fornix of the vagina.

29. A container for in-vitro fertilization of ovocytes and intravaginal culture, said container being of a size and configuration suitable for accommodation in a human vagina, said container comprising a hollow body containing a culture medium suitable for use in fertilization and culture of human ovocytes and having an orifice, said hollow body having rounded inner walls that are smooth over their entire extent, rupturable sealing means closing said orifice and hermetically sealing off the interior of the hollow body containing culture medium, said rupturable sealing means when ruptured permitting the introduction of ovocytes and spermatozoa into the container body, and a closure means cooperable with the container body and adapted to overlie the orifice, and resealing means operatively disposed between the container body and the closure means for hermetically resealing the container after rupture of the rupturable sealing means and introduction of ovocytes and spermatozoa to permit in-vitro fertilization of the ovocytes and intravaginal culture, in combination with a holding device for maintaining the container in a posterior fornix, said holding device comprising a ring and a flexible pouch for receiving the container, said flexible pouch being attached to the ring.

30. Apparatus for in-vitro fertilization of ovocytes and intravaginal culture, comprising an intravaginal container of a size and configuration suitable for accommodation in a vagina, said container comprising a hollow body containing a culture medium suitable for use in fertilization and culture of ovocytes, said hollow body having rounded inner walls that are smooth over their entire extent, a closure means for hermetically sealing the container body, a wall portion of the container body being rupturable, the closure means being adapted to overlie the rupturable wall portion after rupture, and means for penetrating said rupturable wall portion to introduce ovocytes and spermatozoa into the container body containing the culture medium so as to permit in-vitro fertilization and intravaginal culture in the hermetically sealed container, in combination with a holding device for maintaining the container in a posterior fornix, said holding device comprising a ring and a flexible pouch for receiving the container, said flexible pouch being attached to the ring.

* * * * *

UNITED STATES PATENT AND TRADEMARK OFFICE
CERTIFICATE OF CORRECTION

PATENT NO. : 4,902,286

DATED : February 20, 1990

INVENTOR(S) : Claude Ranoux

It is certified that error appears in the above-identified patent and that said Letters Patent is hereby corrected as shown below: In the drawings, sheet 1 (Fig. 1), at ref. 13 (2 instances) the metal element has been changed from circular to square.

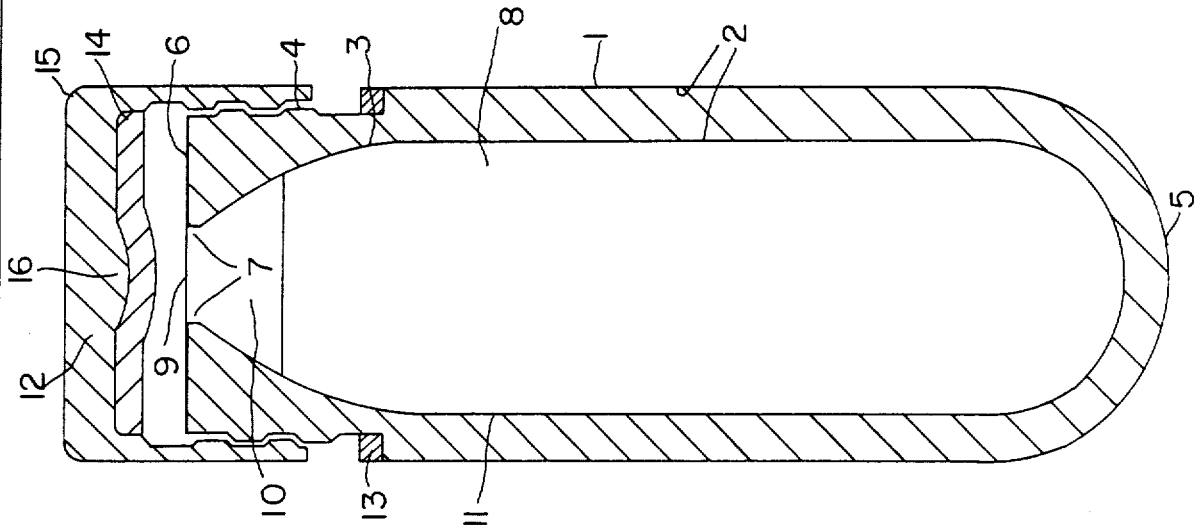

FIG.1

Signed and Sealed this

Twenty-ninth Day of January, 1991

Attest:

HARRY F. MANBECK, JR.

Attesting Officer

Commissioner of Patents and Trademarks